United States Patent [19]

Goldstein et al.

[11] Patent Number: 4,895,716

[45] Date of Patent: Jan. 23, 1990

[54] STABILIZED FORMULATIONS OF GAMMA INTERFERONS

[75] Inventors: Joel D. Goldstein, Brighton; David R. Thatcher, Groton, both of Mass.

[73] Assignee: Biogen, Inc., Cambridge, Mass.

[21] Appl. No.: 59,723

[22] Filed: Jun. 9, 1987

[51] Int. Cl.[4] ............................................. A61K 45/02
[52] U.S. Cl. .................................... 424/85.5; 424/85.4
[58] Field of Search .................. 424/85.4, 85.5, 85.6, 424/85.7

[56] References Cited

U.S. PATENT DOCUMENTS

| 4,252,791 | 2/1981 | Grossberg et al. | 424/85 |
| 4,675,183 | 6/1987 | Kato et al. | 424/85 |
| 4,714,611 | 12/1987 | Yasaburgo et al. | 424/85 |

FOREIGN PATENT DOCUMENTS

| 27573 | 4/1981 | European Pat. Off. . |
| 80879 | 6/1983 | European Pat. Off. . |
| 82481 | 6/1983 | European Pat. Off. . |
| 123291 | 10/1984 | European Pat. Off. . |
| 133767 | 3/1985 | European Pat. Off. . |
| 150067 | 7/1985 | European Pat. Off. . |
| 168008 | 1/1986 | European Pat. Off. . |
| 0177910 | 4/1986 | European Pat. Off. . |

OTHER PUBLICATIONS

Bonnem et al., J. Biol. Response Modifiers, vol. 6, pp. 275–301, 1987.

Sedmak et al., "Stabilization of Interferons", *Texas Reports on Biology and Medicine*, 35, pp. 198–204, (1977).

Sedmak et al., "Thermal and Vortical Stability", *Human Interferon Production and Clinical Use*, pp. 133–152, Plenam Press, (1978).

Sedmak et al., "Procedures for Stabilization of Interferons", *Methods in Enzymology*, 78, pp. 591–595, (1981).

Jameson et al., "Thermal Stability of Freeze Dried Mammalian Interferons", *Cryobiology*, 16, pp. 301–314, (1979).

*Primary Examiner*—Blondel Hazel
*Attorney, Agent, or Firm*—James F. Haley, Jr.; Leon R. Yankwich

[57] ABSTRACT

This invention relates to compositions and methods useful for the stabilization of interferons. More particularly, this invention relates to the formulation of gamma interferons with lactobionic acid in an acetate/glycine buffer.

14 Claims, 1 Drawing Sheet

Lactobionic Acid Formulation, Stored at +20°C

Lactobionic Acid Formulation, Stored at +90°C

Phosphate Buffer Formulation, Stored at -20°C

B.1428

STABILIZED FORMULATIONS OF GAMMA INTERFERONS

TECHNICAL FIELD OF THE INVENTION

This invention relates to compositions and methods useful for the stabilization of interferons. More particularly, this invention relates to formulations for gamma interferons having increased stability in solutions, in frozen and lyophilized forms and in sustained release drug delivery and other pharmaceutical preparations; and which are advantageous in terms of ease of manufacture and maximum concentration attainable per volume of dosage unit. According to this invention, gamma interferons are formulated with lactobionic acid in an acetate/glycine buffer.

BACKGROUND OF THE INVENTION

To realize the considerable clinical potential of interferons ("IFNs"), their the biological activity must be retained during storage and administration. However, the stability of IFNs has proven to be a greater problem than was appreciated from early observations on the stability of crude materials. J. Sedmak et al., "Procedures for Stabilization of Interferons", *Methods in Enzymology*, 78, p. 591 (1981). It is now realized that IFNs in solution can be inactivated by a variety of physical and chemical treatments, and that gamma interferons ("IFN-γs") are particularly pH- and heat-labile. J. Sedmak and S. Grossberg, "Stabilization of Interferons", *Texas Reports on Biology and Medicine*, 35, p. 198 (1977).

Although lyophilization in the presence of serum albumin is a standard stabilizing formulation of IFNs ("Procedures for Stabilization of Interferons", *Methods of Enzymology*, 78, pp. 593–94 (1981)), numerous other agents have been tested, including gelatin, tripeptides, sodium dodecyl sulfate and thioctic acid. J. Sedmak et al., "Thermal and Vortical Stability of Purified Human Fibroblast Interferon", *Human Interferon Production and Clinical Use*, pp. 133–52 (1978); P. Jameson et al., "Thermal Stability of Freeze-Dried Mammalian Interferons", *Cryobiology* 16, pp. 301–14 (1979).

DISCLOSURE OF THE INVENTION

The present invention is based on the discovery that stabilized formulations of IFN-γs are obtained by the inclusion of lactobionic acid therein.

We have found that the formulations described herein are superior to phosphate-buffered serum albumin formulations in terms of ease of manufacture and the maximum concentration attainable per unit volume of the dosage unit; and that they produce increased stability of solutions, frozen forms, lyophilized powders and reconstituted preparations. Moreover, the formulations of our inventions pricipally present IFN-γs in a dimer form, which is the molecular form which predominates in natural, circulating human IFN-γ.

BEST MODE OF CARRYING OUT THE INVENTION

Figure 1:
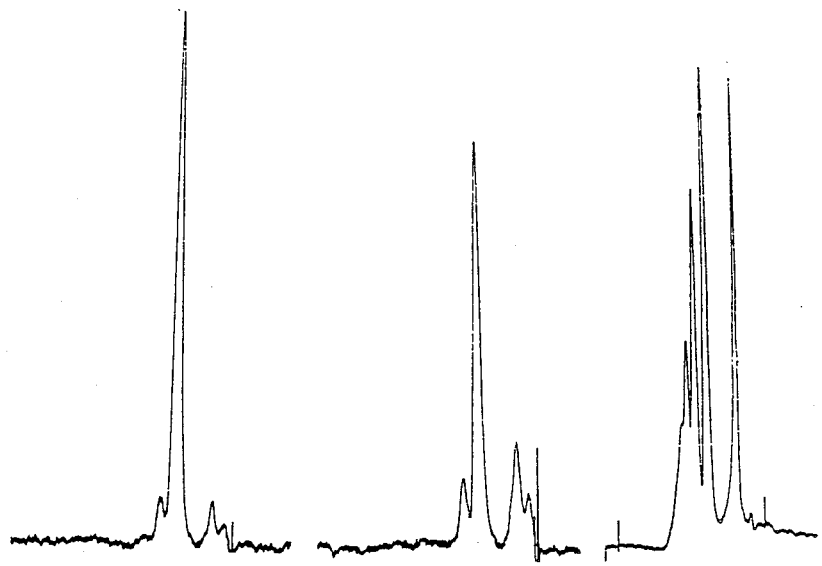
FIG. 1 is a representation of the effect that various formulations have on the aggregation of an IFN-γ upon its reconstitution from lyophilized powder. More specifically, the aggregation of CYS-TYR-CYS recombinant human IFN-γ formulated according to this invention is compared with the aggregation of such IFN-γ formulated in a phosphate buffer.

In order that the invention herein described may be more fully understood, the following detailed description is set forth.

The formulations of this invention contain IFN-γs, lactobionic acid and an acetate/glycine buffer. These formulations may also contain reducing agents and additional elements such as carriers, preservatives, surfactants, amino acids and chelating agents. These formulations may be used to stabilize IFN-γs for the purpose of processing, storage and pharmaceutical administration.

IFN-γs —As used in this application and claims, IFN-γs include all proteins, polypeptides and peptides which are characterized by the biological activity of IFN-γs, for example, natural or recombinant IFN-γs, or derivatives thereof. These include IFN-γ-like compounds from a variety of sources such as natural IFN-γs, recombinant IFN-γs, and synthetic or semi-synthetic IFN-γs.

For example, IFN-γs useful in the compositions and processes of this invention include natural IFN-γs produced constitutively in vitro by established or transformed cell lines and natural IFN-γs produced in vitro by a variety of cells in response to interferon inducers. The IFN-γs useful in the compositions and processes of this invention also include those produced by cloning and expression in various host/ vector systems using recombinant DNA technology. IFN-γs produced according to such processes may be purified by conventional filtration or chromatographic methods.

In the formulations of this invention, the IFN-γs are preferably present in concentrations of between 10μg/ml and 10 mg/ml. Formulations of this invention used in the pharmaceutical administration of IFN-γs, such as sustained release dosage forms, may contain concentrations of IFN-γs in excess of 10 mg/ml.

Lactobionic Acid —Lactobionic acid is an acidic sugar derivative which, in solution, may be a counter-ion to the IFN-γs in the formulations of this invention because of the strongly cationic charge at physiological pH of IFN-γs. The formulations of this invention preferably contain lactobionic acid in concentrations of between 0.05 and 0.5 % (weight/volume).

Acetate/Glycine Buffer —The acetate/glycine buffers used in this invention are used in an amount such that final IFN-γ formulation preferably contains glycine in concentrations of between 0.2 and 5.0 % (weight/volume) and acetate preferably in a concentration of between 0.02 and 0.1M.

Reducing Agents —The compositions according to this invention may also contain sulfur-containing mild reducing agents. The presence of such reducing agents is especially desirable when the IFN-γ to be formulated contains a CYS-TYR-CYS sequence at its N-terminus. When formulating IFN-γs which do not contain such a terminal sequence (e.g., delta-CYS IFN-γ), it is not as useful to include such reducing agents; however, they may still be employed. The concentrations of such reducing agents are not critical, but are generally greater than a two-fold molar excess. Examples of such reducing agents are N-acetylcysteine and tiopronin.

Additional Elements —Other compounds may also be added to the formulations of this invention. For example, when the formulations of this invention are used in the pharmaceutical administration of IFN-γs, such dosage forms may include pharmaceutically acceptable carriers such as human serum albumin, polyvinylpyrrolidone and gelatin. Formulations of this invention also may include preservatives such as benzyl alcohol, phenol and sorbic acid; surfactants such as Tween-20, Tween-80, Pluronic F-68, and bile salts; amino acids such as glycine, alanine, leucine, glutamic acid and aspartic acid; and chelating agents such as citric acid, tartaric acid, gluconic acid, saccharic acid, ethylenediamine tetracetic acid and ascorbic acid.

According to this invention, IFN-γs are preferably formulated by adding lactobionic acid to solutions of IFN-γs in acetate/glycine buffers. This may be achieved by taking solutions of IFN-γs, preferably in the presence of sulfur-containing reducing agents, and exchanging the buffer in which the IFN-γ presently resides for an actetate/glycine buffer by dialysis, diafiltration or gel filtration. The desired pH (preferably 6.0) and protein concentration are then adjusted with an acetate/glycine buffer containing lactobionic acid.

As mentioned above, the formulations of this invention may be used to stabilize IFN-γs for the purpose of processing, storage and pharmaceutical administration. Specifically, when formulated in accordance with this invention, IFN-γs are stable in their initial solutions, in frozen forms or lyophilized powders and in reconstituted solutions. In this regard, IFN-γs formulated according to the present invention may be frozen, lyophilized or otherwise prepared for storage by any means known to one with skill in the art. As compared with phosphatebuffered serum albumin formulations, use of the formulations described herein increases the upper limit of IFN-γ concentrations in bulk formulated solutions. This facilitates the production of dosage forms in excess of 1.5 mg/vial.

Moreover, formulations according to this invention may be used in the pharmaceutical administration of IFN-γs either directly or via a device such as a slow release vehicle or infusion pump. For that purpose, IFN-γs have been shown useful in the treatment of various diseases such as those characterized by tumorigenic or neoplastic cell growth, malignant hematological systemic diseases, viral diseases, rheumatic diseases, carcinomas, sarcomas, myelomas, melanomas, lymphomas, papillomas, degenerative diseases, allergic diseases, asthma and psoriasis. Such diseases include, for example, Crohn's disease, multiple sclerosis, amyotrophic lateral sclerosis, hypernephroma, pseudomyxoma, mastocytosis, immunocytoma, Hodgkin's disease, solid tumors, Schmincke tumor, synovial sarcoma, brochial asthmas, food allergies, psoriasis vulgaris, hepatitis B viral infections, papilloma virus infections, zoster oticus, systemic lupus erythematodes, rheumatoid arthritis, progressive systemic scleroderma, dermatomyosis, psoriasis arthopathica, muscular rheumatism, periarthritis humeroscapularis, panarthritis nodosa, myositis, myogelosis, arthritis uratica, chondrocakinosis and Still's disease.

In this regard, IFN-γs formulated according to the present invention may be administered to patients in any pharmaceutically acceptable dosage form including those which may be administered to patients via a drug delivery device such as a sustained release dosage form, infusion pump, implant or liposome, intravenously, intramuscularly, subcutaneously, intracutaneously, introarticularly, intrasynovially, intrathecally, periostally, or by oral, inhalation or topical routes. IFN-γs formulated according to this invention also may be administered intratumorally, pertitumorally, intralesionally or periolesionally, to exert local as well as systemic therapeutic effects.

In order that the invention described herein may be more fully understood, the following data concerning the effectiveness of formulations of this invention are set forth. It should be understood that these examples are for illustrative purposes only and are not to be construed as limiting this invention in any manner.

In the following examples, the IFN-γ used was CYS-TYR-CYS recombinant human IFN-65 supplied by Biogen S.A., Geneva. The specific activity of Biogen's recombinant human IFN-γ was in the range of 1-3 $\times 10^7$ I.U./mg of protein.

EXAMPLE 1

This Example demonstrates the beneficial effects that the addition of lactobionic acid has on reconstituting lyophilized formulations of IFN-γY.

Formulated IFN-γ was dispensed in 1 ml portions into 3ml vials and frozen at −70° C. Vials were then transferred to a Virtis lyophilizer, shelf temperature -45° C. A vacuum of 50μ was applied and after 6 hours the shelf temperature raised to 0° C over a period of 6 hours. Secondary drying was accomplished by raising the temperature to 20° C over a period of 10 hours. After completion of the cycle, the drying chamber was filled with oxygen-free nitrogen and the vials stoppered.

Vials were stored either at room temperature or exposed to 50° C. for 7 hours before analysis. The physical appearance of the cakes was recorded. Lyophilized material was then reconstituted with 1 ml of sterile water. The reconstitution time was recorded and the degree of clarity estimated visually. The results are summarized in Table I. Unlike lyophilization of IFN-γs formulated with only the acetate/ glycine buffer, all lactobionic acid formulations gave acceptable cakes which reconstituted well and which were not susceptible to temperature deterioration.

TABLE I

| FORMULATIONS: ALL 1 MG/ML RECOMBINANT IFN-γ | | | |
|---|---|---|---|
| FORMULATION | CAKE APPEARANCE | RECONSTITUTION TIME (SEC.) | TURBIDITY |
| NO STABILIZER | | | |
| 0.1 M sodium acetate/ 2% glycine buffer (Buffer). | Good | 12-20 | Clear and some flecks |
| Buffer (7 hours at 50° C). | Good | 12-20 | Hazy |
| LACTOBIONIC ACID (LB) STABILIZER | | | |
| Buffer and 0.5% LB. | Good | 20-40 | Clear |
| Buffer and 0.5% LB (7 hours at 50° C). | Good | 20-40 | Clear |
| Buffer, 0.5% LB and | Good | 20-40 | Clear |

TABLE I-continued

| FORMULATION | CAKE APPEARANCE | RECONSTITUTION TIME (SEC.) | TURBIDITY |
|---|---|---|---|
| 0.01% N—acetylcysteine. Buffer, 0.5% LB and 0.01% N—acetylcysteine (7 hours at 50° C.). | Good | 20–40 | Clear |
| Buffer, 0.5% LB and 0.01% tiopronin. | Good | 20–40 | Clear |

FORMULATIONS: ALL 1 MG/ML RECOMBINANT IFN-γ

EXAMPLE 2

This Example demonstrates the temperature stabilizing effect that formulations of this invention have on the antiviral activity of IFN-γ.

Two experimental formulations containing 1mg/ml IFN-γ were prepared:
(a) 0.01% tiopronin, 0.25% lactobionic acid, 0.05125M sodium acetate and 2 % glycine, at pH 6.0;
0.01% N-acetylcysteine, 0.25% lactobionic acid, 0.05125 M sodium acetate and 2 % glycine, at pH 6.0.

These samples were lyophilized and the vials were placed in a temperature controlled water bath at 50° C, programmed to increase the temperature at a rate of 2° C/hour. Samples were taken when the temperature reached 60° C, 70° C, 80° C and 90° C. Samples were then reconstituted in 1 ml of deionized water and analyzed for antiviral activity. The results are summarized in Table II. All samples reconstituted to clear solutions. Only in samples heated to 90° C was there any evidence for loss in specific activity.

TABLE II

| SAMPLE | MAXIMUM INCUBATION TEMPERATURE (°C.) | ACTIVITY ($\times 10^7$ μ/mg) |
|---|---|---|
| [0.01% tiopronin, 0.25% lactobionate, 0.05125 M acetate and 2% glycine] | 20 (control) | 1.02 |
| | 50 | 1.09 |
| | 60 | 0.97 |
| | 70 | 0.92 |
| | 80 | 1.06 |
| | 90 | 0.65 |
| [0.01% N—acetylcysteine, 0.25% lactobionate, 0.05125 M acetate and 2% glycine] | 20 (control) | 1.68 |
| | 50 | 1.45 |
| | 60 | 1.37 |
| | 70 | 1.50 |
| | 80 | 1.45 |
| | 90 | 0.75 |

EXAMPLE 3

This Example illustrates the effect that formulations of this invention have on the existence of noncovalent interactions in reconstituted IFN-γ.

Analysis of the quaternary structure of IFN-γ has shown that upon reconsitution from lyophilized powder heated at 50° C for 7 hours, IFN-γ formulated with only an acetate/glycine buffer had 15% dimeric material, whereas IFN-γ in a 0.25% lactobionic acid 0.01% N-acetylcysteine formulation contained 73% dimeric IFN-γ. Additionally, Figure I compares a Superose 12 HPLC trace of a final (90° C.) sample from the temperature stability test (see Example 2) with a control (20° C.) sample from the same test and a sample of IFN-γ formulated with a phosphate buffer stored at −20° C. No higher order aggregates were detected in the lactobionic formulation, with or without pre-heating, unlike the phosphate buffer formulation which had significant levels of higher order aggregates. Such higher order aggregates have also been observed in reconstituted IFN-γ/serum albumin formulations.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:
1. A composition which comprises IFN-γ, lactobionic acid and an acetate/glycine buffer.
2. The composition according to claim 1, further comprising a sulfur-containing mild reducing agent.
3. The composition according to claim 2 wherein the sulfur-containing mild reducing agent is selected from the group consisting of N-acetylcysteine and tiopronin.
4. The composition according to claim 1, 2 or 3, further comprising at least one compound selected from the group consisting of preservatives, carriers, amino acids, chelating agents and surfactants.
5. The composition according to claim 1, 2 or 3, wherein the IFN-γ is selected from the group consisting of natural IFN-γs, recombinant IFN-γs and synthetic IFN-γs.
6. The composition according to claim 1, 2 or 3, wherein the IFN-γ contains a CYS-TYR-CYS residue at its N-terminus.
7. A composition comprising from about 10 μg/ml to 10 mg/ml of IFN-γ, from about 0.05% to 0.5% (weight/volume) of lactobionic acid, from about 0.2% to 5.0% (weight/volume) of glycine and from about 0.02M to 0.1M acetate.
8. The composition according to claim 7 further comprising greater than a two-fold molar excess of a sulfur-containing mild reducing agent.
9. A method for stabilizing IFN-γ by formulating said IFN-γ in the presence of lactobionic acid and an acetate/glycine buffer.
10. The method according to claim 9, wherein the IFN-γ is also formulated in the presence of a sulfur-containing mild reducing agent.
11. The method according to claim 10, wherein the sulfur-containing mild reducing agent is selected from the group consisting of N-acetylcysteine or tiopronin.
12. The method according to claim 9, 10 or 11, wherein IFN-γ is also formulated in the presence of at least one compound selected from the group consisting of preservatives, carriers, amino acids, chelating agents and surfactants.
13. The method according to claim 9, 10 or 11, wherein the IFN-γ is selected from the group consisting of natural IFN-γs, recombinant IFN-γs and synthetic IFN-γs.
14. The method according to claim 9, 10 or 11, wherein the IFN-γ contains a CYS-TYR-CYS residue at its N-terminus.

* * * * *